US011335456B2

(12) United States Patent
Wu et al.

(10) Patent No.: US 11,335,456 B2
(45) Date of Patent: May 17, 2022

(54) SENSING DEVICE FOR MEDICAL FACILITIES (71) Applicant: SHANGHAI UNITED IMAGING INTELLIGENCE CO., LTD., Shanghai (CN)

(72) Inventors: Ziyan Wu, Lexington, MA (US); Srikrishna Karanam, Brighton, MA (US); Arun Innanje, Lexington, MA (US); Shanhui Sun, Lexington, MA (US); Abhishek Sharma, Boston, MA (US); Yimo Guo, Lexington, MA (US); Zhang Chen, Brookline, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 68 days.

(21) Appl. No.: 16/860,901

(22) Filed: Apr. 28, 2020

(65) Prior Publication Data
US 2021/0158937 A1 May 27, 2021

Related U.S. Application Data (60) Provisional application No. 62/941,203, filed on Nov. 27, 2019.

(51) Int. Cl.
*G16H 30/40* (2018.01)
*A61B 5/00* (2006.01)
(Continued)

(52) U.S. Cl.
CPC ........... *G16H 30/40* (2018.01); *A61B 5/0035* (2013.01); *A61B 5/70* (2013.01); *G06K 9/6217* (2013.01);
(Continued)

(58) Field of Classification Search
CPC .......... G16H 30/40; G06T 17/00; G06T 7/90; G06T 7/0012; G06T 2207/30004;
(Continued)

(56) References Cited

U.S. PATENT DOCUMENTS 8,880,765 B2 * 11/2014 Melvin, Jr. ......... H02J 13/0075
710/301
2013/0250050 A1 * 9/2013 Kanaujia .............. H04N 13/106
348/42
(Continued)

FOREIGN PATENT DOCUMENTS

CN 107334487 A 11/2017
CN 107924564 A 4/2018
(Continued)

OTHER PUBLICATIONS

Machine Translation of CN107334487 (Year: 2017).*
(Continued)

*Primary Examiner* — Sing-Wai Wu
(74) *Attorney, Agent, or Firm* — Zhong Law, LLC (57) ABSTRACT A medical system may utilize a modular and extensible sensing device to derive a two-dimensional (2D) or three-dimensional (3D) human model for a patient in real-time based on images of the patient captured by a sensor such as a digital camera. The 2D or 3D human model may be visually presented on one or more devices of the medical system and used to facilitate a healthcare service provided to the patient. In examples, the 2D or 3D human model may be used to improve the speed, accuracy and consistency of patient positioning for a medical procedure. In examples, the 2D or 3D human model may be used to enable unified analysis of the patient's medical conditions by linking different scan images of the patient through the 2D or 3D human model. In examples, the 2D or 3D human model may (Continued)

be used to facilitate surgical navigation, patient monitoring, process automation, and/or the like.

20 Claims, 5 Drawing Sheets (51) Int. Cl.
    *G06K 9/62* (2006.01)
    *G06T 7/00* (2017.01)
    *G06T 7/50* (2017.01)
    *G06T 7/70* (2017.01)
    *G06T 17/00* (2006.01)
    *G06V 10/40* (2022.01)
    *G06T 7/90* (2017.01)
    *G06T 17/20* (2006.01)
    *G16H 10/60* (2018.01)
    *G16H 30/20* (2018.01)
    *G06V 10/42* (2022.01)
    *G06V 20/64* (2022.01)
    *G06V 40/10* (2022.01)
    *G06V 40/20* (2022.01)

(52) U.S. Cl.
    CPC ......... *G06K 9/6256* (2013.01); *G06K 9/6265* (2013.01); *G06T 7/0012* (2013.01); *G06T 7/50* (2017.01); *G06T 7/70* (2017.01); *G06T 7/90* (2017.01); *G06T 17/00* (2013.01); *G06T 17/20* (2013.01); *G06V 10/40* (2022.01); *G06V 10/42* (2022.01); *G06V 20/64* (2022.01); *G06V 40/10* (2022.01); *G06V 40/20* (2022.01); *G16H 10/60* (2018.01); *G16H 30/20* (2018.01); *G06T 2200/08* (2013.01); *G06T 2207/10024* (2013.01); *G06T 2207/20081* (2013.01); *G06T 2207/20084* (2013.01); *G06T 2207/30004* (2013.01); *G06T 2207/30196* (2013.01); *G06V 2201/033* (2022.01)

(58) Field of Classification Search
    CPC ...... G06T 2200/08; G06T 2207/10024; G06K 9/00362; G06K 9/46
    See application file for complete search history.

(56) References Cited

U.S. PATENT DOCUMENTS

2015/0196780 A1* 7/2015 Tijs ..................... A61N 5/1049
                                                            600/1
2017/0332946 A1 11/2017 Kikkeri

FOREIGN PATENT DOCUMENTS

| CN | 108175503 A | 6/2018 |
| CN | 109247940 A | 1/2019 |
| CN | 109937012 A | 6/2019 |

OTHER PUBLICATIONS

Machine Translation of CN109247940 (Year: 2019).*
Wei et al., "Convolutional Pose Machines" CVF, 2016, pp. 4724-4732.
Zhou et al., "Towards 3D Human Pose Estimation in theWild: aWeakly-supervised Approach", CVF, 2017, pp. 398-407.
Zimmermann et al., "3D Human Pose Estimation in RGBD Images for Robotic Task Learning",arXiv:1803.02622v2 [cs.CV] Mar. 13, 2018, pp. 1-7.
International Application No. PCT/CN2020/131793, International Search Report and Written Opinion dated Feb. 25, 2021, 10 pages.
Guler et al., "DensePose: Dense Human Pose Estimation in the Wild", 2018, CVF, pp. 7297-7306.
Arnab et al., "Exploiting Temporal Context for 3D Human Pose Estimation in the Wild", 2019, CVF, pp. 3395-3404.
Bahdanau et al., "Neural Machine Translation by Jointly Learning to Align and Translate", ICLR, 2015, arXiv:1409.0473v7 [cs.CL], pp. 1-15.
Belghit et al., "Vision-Based Pose Estimation for Augmented Reality: A Comparison Study", IEEE, 2018, pp. 1-8.
Bogo et al., "Keep It SMPL: Automatic Estimation of 3D Human Pose and Shape from a Single Image", Computer Vision and Pattern Recognition, 2016, pp. 561-578.
Cao et al., "Realtime Multi-Person 2D Pose Estimation Using Part Affinity Fields", CVF, 2017, pp. 7291-7299.
Chen et al., 3D Human Pose Estimation + 2D Pose Estimation + Matching, CVF, 2016, pp. 7035-7043.
Chen et al., "Synthesizing Training Images for Boosting Human 3D Pose Estimation", arXiv:1604.02703v6 [cs.CV] Jan. 5, 2017, pp. 4321-4330.
Chen et al., "Weakly-Supervised Discovery of Geometry-Aware Representation for 3D Human Pose Estimation", CVF, 2019, pp. 10895-10904.
Liu et al., "PKU-MMD: A Large Scale Benchmark for Continuous Multi-Modal Human Action Understanding", arXiv:1703.07475v2 [cs.CV] Mar. 28, 2017, pp. 1-10.
Deprelle et al., "Learning Elementary Structures for 3D Shape Generation and Matching", arXiv:1908.04725v2 [cs.CV] Aug. 14, 2019, pp. 1-11.
Groueix et al., "3D-Coded: 3D Correspondences by Deep Deformation", CVF, 2018, pp. 1-17.
Gupta et al., "3D Pose from Motion for Cross-View Action Recognition via Non-linear Circulant Temporal Encoding", CVF, 2014, pp. 1-8.
He et al., "Deep Residual Learning for Image Recognition", CVF, 2015, pp. 770-778.
He et al., "Identity Mappings in Deep Residual Networks", arXiv:1603.05027v3 [cs.CV] Jul. 25, 2016. pp. 1-15.
Jahangiri et al., "Generating Multiple Diverse Hypotheses for Human 3D Pose Consistent with 2D Joint Detections", IEEE, 2017, pp. 805-814.
Hao Jiang, "3D Human Pose Reconstruction Using Millions of Exemplars", International Conference on Pattern Recognition, 2010, pp. 1674-1677.
Johnson et al., "Clustered Pose and Nonlinear Appearance Models for Human Pose Estimation", BMVC, 2010, pp. 1-11.
Kadkhodamohammadi et al., "A Multi-View RGB-D Approach for Human Pose Estimation in Operating Rooms," IEEE, 2017, pp. 363-372.
Kanazawa et al., "End-To-End Recovery of Human Shape and Pose", CVF, 2017, pp. 7122-7131.
Kanazawa et al., "Learning 3D Human Dynamics from Video", CVF, 2019, pp. 5614-5623.
Kocabas et al., "Self-Supervised Learning of 3D Human Pose Using Multi-View Geometry", CVF, 2019, pp. 1077-1086.
Kohli et al., "Key Developments in Human Pose Estimation for Kinect", Advances in Computer Vision and Pattern Recognition, 2013, pp. 63-70.
Kolotouros et al., "Convolutional Mesh Regression for Single-Image Human Shape Reconstruction", CVF, 2019, pp. 4501-4510.
Lassner et al., "Unite the People: Closing the Loop Between 3D and 2D Human Representations", CVF, 2017, pp. 6050-6059.
Levine et al., "End-To-End Training of Deep Visuomotor Policies", Journal of Machine Learning Research 17, 2016, pp. 1-40.
Liang et al., "Shape-Aware Human Pose and Shape Reconstruction Using Multi-View Images", CVF, 2019, pp. 4352-4362.
Lin et al., "Microsoft COCO: Common Objects in Context", Springer International Publishing Switzerland, 2014, pp. 740-755.
Looper et al., "MoSh: Motion and Shape Capture from Sparse Markers", ACM Transactions on Graphics, vol. 33, No. 6, 2014, pp. 1-13.
Looper et al., "SMPL: A Skinned Multi-Person Linear Model", ACM Transactions on Graphics, 2015, pp. 1-16.

(56) References Cited

OTHER PUBLICATIONS

Martinez et al., "A Simple Yet Effective Baseline for 3D Human Pose Estimation", CVF, 2017, pp. 2640-2649.
Martinez-Gonzalez et al., "Reall-time Convolutional Networks for Depth-Based Human Pose Estimation", IDIAP Research Institute, 2018, pp. 1-7.
Mehta et al., "VNect: Real-time 3D Human Pose Estimation with a Single RGB Camera", ACM Transactions on Graphics, vol. 36, No. 4, 2017, pp. 1-14.
Moeslund et al., "A Survey of Computer Vision-Based Human Motion Capture" Computer Vision and Image Understanding 81, 2001, pp. 231-268.
Moeslund et al., "A Survey of Advances in Vision-Based Human Motion Capture", Elsevier, 2006, pp. 90-126.
Newell et al., "Stacked Hourglass Networks for Human Pose Estimation", arXiv:1603.06937v2 [cs.CV] Jul. 26, 2016, pp. 1-17.
Obdrzalek et al., "Accuracy and Robustness of Kinect Pose Estimation in the Context of Coaching of Elderly Population", IEEE, 2012, pp. 1188-1193.
Paszke et al., "Automatic Differentiation in PyTorch" 31st Conference on Neural Information Processing Systems, 2017, pp. 1-4.
Pavlakos et al., "Ordinal Depth Supervision for 3D Human Pose Estimation", CVF, 2018, pp. 7307-7316.
Pavlakos et al., "Coarse-To-Fine Volumetric Prediction for Single-Image 3D Human Pose", CVF, 2017, pp. 7025-7034.
Peng et al., "Jointly Optimize Data Augmentation and Network Training Adversarial Data Augmentation in Human Pose Estimation", CVF, 2018, pp. 2226-2234.
Rhodin et al., "Neural Scene Decomposition for Multi-Person Motion Capture", CVF, 2019, pp. 7703-7713.
Rhodin et al., "Unsupervised Geometry-Aware Representation for 3D Human Pose Estimation", CVF 2018, pp. 1-18.
Rogez et al., "MoCap-Guided Data Augmentation for 3D Pose Estimation in the Wild", Computer Vision and Pattern Recognition, 2016, pp. 1-9.
Sarafianos et al., "3D Human Pose Estimation: A Review of the Literature and Analysis of Covariates" Elsevier, Computer Vision and Image Understanding, 2016, pp. 1-20.
Sharma et al., "Monocular 3D Human Pose Estimation by Generation and Ordinal Ranking", CVF, 2019, pp. 2325-2334.
Sun et al., "Integral Human Pose Regression" CVF, 2018, pp. 1-17.
Sung et al., "Unstructured Human Activity Detection from RGBD Images", IEEE, 2012, pp. 1-8.
Varol et al., "Learning from Synthetic Humans", CVF, 2017, pp. 109-117.
Wandt et al., "RepNet: Weakly Supervised Training of an Adversarial Reprojection Network for 3D Human Pose Estimation", CVF, 2019, pp. 7782-7791.

* cited by examiner

SENSING DEVICE FOR MEDICAL FACILITIES

CROSS-REFERENCE TO RELATED APPLICATIONS

This application claims the benefit of Provisional U.S. Patent Application No. 62/941,203, filed Nov. 27, 2019, the disclosure of which is incorporated herein by reference in its entirety.

BACKGROUND

The quality of healthcare services provided to a patient largely depends on the amount of information available to the patient and medical professionals such as doctors rendering the services. For example, with radiation therapy and medical imaging, success often hinges upon the ability to place and maintain a patient in a desirable position so that the treatment or scan can be performed in a precise and accurate manner. Having up-to-date knowledge about the patient's physical characteristics (e.g., height, body shape, pose, etc.) in these situations may offer many benefits including, for example, faster and more accurate positioning of the patient in accordance with a scan or treatment protocol, less manual work, more consistent results, etc. The knowledge about the patient's physical characteristics can also be used to aggregate different medical records of the patient (e.g., based on common attributes of the patient present in the medical records and/or the identity of the patient), and derive a comprehensive view of the patient's diagnostic and treatment history.

In other example situations such as during a surgical procedure, information about a patient's physiques, movements, and/or positions may offer insight and guidance for both treatment planning and execution. The information may be utilized, for instance, to locate and navigate around a treatment site of the patient. When visually presented in real-time, the information may also provide means for monitoring the state of the patient during the procedure.

With the advancement of technologies in areas such as computer vision and artificial intelligence, it is desirable to utilize these technologies to acquire patient information in an automatic and real-time manner, and to improve the quality of healthcare services utilizing the acquired information.

SUMMARY

Described herein are systems, methods and instrumentalities for providing healthcare services to a patient using a medical system. The medical system may comprise a modular and extensible sensing device capable of generating, in real-time, a two-dimensional (2D) or three-dimensional (3D) human model and a representation thereof for a patient based on at least one image of the patient captured by one or more sensors. The sensing device may comprise or be coupled to these sensors. The sensing device may comprise one or more processors configured to receive the at least one image of the patient from the sensors. In response to receiving the at least one image, the sensing device (e.g., the one or more processors of the sending device) may analyze the image to extract a plurality of features (e.g., feature vectors) that is representative of one or more anatomical characteristics of the patient and estimate the 2D or 3D human model of the patient based on the features. The 2D or 3D human model of the patient may include, for example, a parametric human body model and the representation of the 2D or 3D model may include a 2D or 3D mesh of the patient.

Once generated, the 2D or 3D human model of the patient and/or its representation may be transmitted to one or more other devices of the medical system, for example, together with the at least one image of the patient captured by the one or more sensors. The 2D or 3D human model and/or its representation may be used to improve one or more aspects of the healthcare services provided to the patient including, for example, patient positioning, patient monitoring, scan image unification and analysis, surgical navigation, etc.

The one or more sensors described herein may include a digital camera, a red-green-blue (RGB) sensor, a depth sensor, a RGB plus depth (RGB-D) sensor, a thermal sensor such as infrared (FIR) or near-infrared (NIR) sensor, etc. As such, the at least one image of the patient captured by the sensors may include a photo of the patient captured by the digital camera or an RGB or thermal image captured by a corresponding sensor.

The sensing device may be modular and extensible and may comprise one or more slots each including at least one of a power connector or a communication interface circuit. Each of the slots may be configured to host a respective set of sensors or processors configured to work with a respective imaging modality or a respective patient. The communication interface circuit may be configured to transmit or receive information on behalf of the respective sensors or processors hosted in the respective slot. The power connector may be configured to provide power to the respective set of sensors or processors hosted in the respective slot. As such, the sensing device may be capable of working with different types of downstream devices and/or different application requirements, for example, by increasing or decreasing the number of sensors or processors included in the sensing device.

The sensing device may be calibrated with other devices in the medical system. For example, the one or more processors of the sensing device may be configured to determine a spatial relationship between a first coordinate system associated with the sensing device and a second coordinate system associated with a medical device such as a medical scanner. This way, the representation of the 2D or 3D human model of the patient generated by the sensing device may be used together with scan images obtained from other imaging modalities (e.g., to align the scan images with the representation of the human model), thus enabling unified analysis of the patient's medical records obtained from different sources. The 2D or 3D human model or its representation may also be used to improve the speed, accuracy and consistency of patient positioning relating to a medical procedure, to facilitate surgical navigation and patient monitoring, etc.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
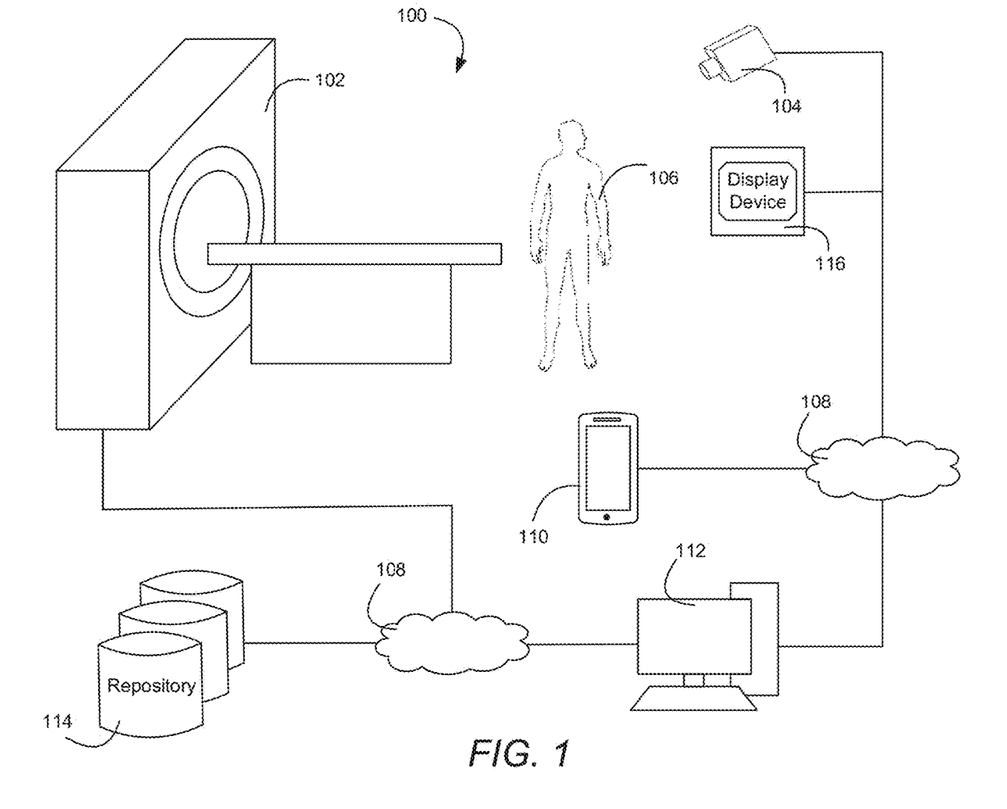
FIG. 1 is a simplified block diagram illustrating an example medical system as described herein.

FIG. 1 is a diagram illustrating an example system 100 for providing healthcare services in a medical environment or at a medical facility, such as in a hospital. The healthcare services may include, for example, a medical scan or imaging procedure conducted using a medical scanner 102 (e.g., a computer tomography (CT) scanner, a magnetic resonance imaging (MRI) machine, a positron emission tomography (PET) scanner, an X-ray machine, etc.), a radiation treatment procedure delivered through a medical linear accelerator (LINAC) (not shown), or a surgical procedure performed in an operating room. The system 100 may include at least one sensing device 104 (e.g., an image capturing device) configured to capture images of a patient 106 (or an object 106) in or around the medical environment (e.g., in front of the medical scanner 102, lying on a scan or treatment bed, etc.). In examples, the sensing device 104 may be configured to detect the presence of the patient 106 using a sensor such as a motion, radar, or light sensor, and capture the images of the patient in response to detecting the patient. In examples, the sensing device 104 may not be configured to automatically detect the presence of the patient 106, but may be controlled (e.g., manually controlled, remotely controlled, programmed, etc.) to capture the images of the patient, for example, in response to receiving a control signal instructing the sensing device to do so.

In examples, the sensing device 104 may comprise one or more sensors including one or more cameras (e.g., digital color cameras, 3D cameras, etc.), one or more red, green and blue (RGB) sensors, one or more depth sensors, one or more RGB plus depth (RGB-D) sensors, one or more thermal sensors such as infrared (FIR) or near-infrared (NIR) sensors, one or more motion sensors, one or more radar sensors, and/or other types of image capturing circuitry configured to generate images (e.g., 2D images or photos) of a person, object or scene. Depending on the type of sensors or image capturing circuits used, the images generated by the sensing device 104 may include, for example, one or more photos of the patient taken by a camera, one or more thermal images of the patient generated by a thermal sensor, one or more radar images of the patient produced by a radar sensor, and/or the like. The sensors of the sensing device 104 may be configured to capture the images of the patient, object or scene in response to detecting the patient, object or scene, based on a preconfigured schedule or time interval, or upon receiving a control signal triggering the image capturing.

In examples, the sensing device 104 may be configured to be communicatively coupled to sensors (e.g., cameras) that already exist in the medical system 100 (e.g., sensors external to the sensing device 104), and to receive and process the images captured by these sensors as if the images are captured by internal sensors of the sensing device 104. For instance, the medical system 100 may already include sensors configured for surveillance, diagnostic or treatment purposes. These sensors may be capable of capturing images of a patient, an object or a scene present in the medical system 100 in response to detecting the patient, object or scene, based on a preconfigured schedule or time interval, or upon receiving a control signal triggering the image capturing. The sensors may also have the capability to transmit the captured images (e.g., raw imagery data comprising pixel information) to a receiving device in the medical system 100, for example, through a communication interface. In at least these scenarios, the sensing device 104 may be added to the medical system 100, e.g., as a receiving device of the images produced by the sensors, and obtain information from the images that may be used to improve the quality of services provided by the medical system 100, as described herein. The sensing device 104 may transmit the information obtained from the images (e.g., in the form a 2D or 3D human model or a representation thereof) to a downstream device or application, for example, together with the imagery data originally received from the sensors.

The sensing device 104 may be installed or placed in various locations of the medical system 100 such as inside a scan room, inside a treatment room, inside an operation room, around a registration desk, in a hallway, on the medical scanner 102, on a ceiling, near a doorway, on a wall, etc. From these locations, the sensing device 104 may capture images of a patient, an object or a scene that is in the field of view (FOV) of the sensing device (e.g., from a certain viewpoint or viewing angle). The FOV of the sensing device 104 may be adjusted (e.g., manually or automatically by sending a control signal to the sensing device) so that multiple images may be taken from different viewpoints or viewing angles.

In examples, the sensing device 104 may be a portable or mobile device, in which case the sensing device may be placed or hosted (e.g., placed on a shelf, attached to a hanging mount, etc.) at the various locations described above and may be moveable from one location to another. In examples, the sensing device 104 may be physically connected to (e.g., be wired together with) a location or another device of the medical system 100, in which case the sensing device may operate as an integral part of the connected device. And although only one sensing device 104 is depicted in FIG. 1, the medical system 100 may include multiple sensing devices each located at a respective location and having a respective FOV.

The sensing device 104 may include a functional unit configured to process the images generated by the sensors described herein (e.g., sensors comprised in the sensing device and/or preexisting sensors that are external to the sensing device). The functional unit may be coupled to the sensors (e.g., via a wired or wireless communication link) and configured to receive images from the sensors (e.g., via a push mechanism). The functional unit may also be configured to retrieve images from the sensors (e.g., via a pull mechanism), for example, on a periodic basis or in response to receiving a control signal instructing the functional unit to retrieve the images. In examples, the functional unit may be configured to receive a notification from the sensors when an image has become available and to retrieve the image in response to receiving the notification.

The images captured by the sensors may include two-dimensional (2D) or three-dimensional (3D) images depicting a patient, an object or a scene present in a medical environment. Each of the 2D or 3D images may comprise a plurality of pixels, lines, and/or vertices. The functional unit may be configured to analyze these images (e.g., at a pixel level) and generate a 2D or 3D model (e.g., a parametric model such as one based on a skinned multi-person linear (SMPL) model) of the patient, object or scene depicted in the images, for example, using a neural network (e.g., a convolutional neural network). The 2D or 3D model generated by the functional unit may include one or more 2D keypoints, one or more 3D keypoints, one or more parameters (e.g., a set of 72 shape and/or pose parameters) for constructing the model, and/or other information relating to a 2D or 3D representation of the patient, object or scene. The 2D or 3D model may be represented, for example, by one or more of a 2D mesh, a 3D mesh, a 2D contour, a 3D contour, etc. to indicate the pose, shape and/or other anatomical characteristics of a patient and thereby to facilitate a plurality of downstream medical applications and services for the patient including, for example, patient positioning, medical protocol design, unified or correlated diagnoses and treatments, medical environment monitoring, surgical navigation, etc. For ease of description, when a 2D or 3D human model of a patient or a 2D or 3D model of an object or scene is referred to herein, it should be interpreted to include not only the model itself but also a representation of the model in any, graphical or visual form.

In examples, the sensing device 104 may function as an edge device (e.g., with limited computation and/or storage capacities), and may pass one or more computation and/or storage tasks (e.g., all computation and/or storage tasks) to a server device. The server device may be a network-based (e.g., cloud-based) server device and may be configured to, upon completing a computation task requested by sensing device 104, provide the computation results (e.g., a recovered human 3D mesh model) to other devices of the medical system 100 including the sensing device 104 for further processing and/or delivery.

The sensing device 104 may include a communication circuit configured exchange information with one or more other devices of the medical system 100, for example, over a communication network 108. The communication network 108 may be a wired or a wireless network, or a combination thereof. For example, the communication network 108 may be established over a public network (e.g., the Internet), a private network (e.g., a local area network (LAN), a wide area network (WAN)), etc.), a wired network (e.g., an Ethernet network), a wireless network (e.g., an 802.11 network, a network, etc.), a cellular network (e.g., a Long Term Evolution (LTE) or 5G network), a frame relay network, a virtual private network (VPN), a satellite network, and/or a telephone network. The communication network 108 may include one or more network access points. For example, the communication network 108 may include wired and/or wireless network access points such as base stations and/or internee exchange points through which one or more components of the medical system 100 may be connected to exchange data and/or other information. Such exchange may utilize routers, hubs, switches, server computers, and/or any combination thereof.

The communication circuit of the sensing device 104 may be configured to receive imagery data produced by the sensors described herein and may transmit, e.g., directly from the sensing device 104 and/or via an edge server, one or more data streams carrying the 2D or 3D human model of a patient or object generated by the sensing device to a receiving device. In addition to the 2D or 3D model, the one or more data streams may also include the original imagery data (e.g., raw images comprising pixels of information) produced by the sensors. The original imagery data may include, for example, RGB data produced by a RGB sensor, depth data produced by a depth sensor, RGB plus depth (RGB-D) data from a RGB-D sensor, infrared (IR) data from an IR sensor, etc. The original imagery data may be used by a downstream device or application for various purposes including, e.g., verifying, reconstructing, or refining the 2D or 3D human model generated by the sensing device, comparing or combining the imagery data with other medical images or scans, etc.

The medical system 100 may include a programming device 110 configured to configure and/or control one or more of the medical scanner 102 or the sensing device 104. For example, the programming device 110 may be configured to initialize and modify one or more operating parameters of the medical scanner 102 or the sensing device 104 such as a resolution at which an image is captured, a frequency for data exchange to and from the sensing device 104 (e.g., frequency for image transmission or retrieval), a frame or bit rate associated with the data exchange, a duration of data storage on the sensing device, etc. The programming device 110 may also be configured to control one or more aspects of the operation of the medical scanner 102 or the sensing device 104 including, e.g., triggering a calibration operation for the devices, providing calibration parameters such as those relating to the spatial relationship between different coordinate systems to the devices, adjusting the direction or orientation of a sensor, zooming in or zooming out a sensor, triggering a system reset, etc. The programming device 110 may include a mobile device such a smart phone, a tablet, or a wearable device. The programming device 110 may include a desktop computer, a laptop computer, and/or the like. The programming device 110 may be configured to communicate with the medical scanner 102 and/or the sensing device 104 over the communication network 108. The programming device 110 may receive information and/or instructions from a user (e.g., via a user interface implemented on the programming device), and send the received information and/or instructions to the medical scanner 102 or the sensing device 104 via the communication network 108.

The medical system 100 may further include a processing device 112 configured to receive one or more data streams from the sensing device 104 and/or a device performing computation or storage tasks on behalf of the sensing device 104. The processing device may be co-located with the sensing device 104 (e.g., in a same room) or be located remotely from the sensing device 104 (e.g., in a control room or processing center away from where the sensing device 104 is located). The processing device 112 may be communicatively coupled to other devices in the medical system 100 including the sensing device 104, The processing device 112 may comprise a general-purpose computer, a special-purpose computer, one or more computation and storage units, a cloud-based platform, and/or the like. Merely by way of example, a cloud-based platform referred to herein may include a private cloud, a public cloud, a hybrid cloud, a community cloud, a distributed cloud, an inter-cloud, a multi-cloud, and/or the like. Further, although the processing device 112 is depicted in FIG. 1 as a separate device from the medical scanner 102, the applicability of the examples provided herein is not limited to such a configuration. For example, the processing device 112 may be a part of (e.g., comprised in) the medical scanner 102 and may still be capable of performing the various functions described herein.

The one or more data streams received by the processing device 112 may include a 2D or 3D model of a patient, an object, or a scene generated by the sensing device 104 and/or imagery data (e.g., raw or original imagery data) produced by a sensor. As described herein, the 2D or 3D model may be generated by the sensing device 104 or a server device performing computation or storage tasks on behalf of the sensing device 104. Once received, the 2D or 3D model may be used by the processing device 112 to assist with various aspects of healthcare services. For example, the processing device 112 may also be coupled to a repository 114 configured to store patient medical records including basic patient information, scan images of the patients obtained through other imaging modalities (e.g., CT, MR, X-ray, SPECT, PET, etc.) of the medical system 100 at different times, diagnostic and/or treatment history of the patients, etc. The processing device 112 may retrieve all or a subset of the medical records for a patient from the repository 114 and analyze the retrieved medical records in conjunction with the 2D or 3D model of the patient provided by the sensing device 104. The processing device 112 may also receive (e.g., in real-time) a scan image of the patient produced by the medical scanner 102, and analyze the received scan image in conjunction with the 2D or 3D model of the patient provided by the sensing device 104. For instance, the processing device 112 may receive a scan image of the patient from the repository 114 or the medical scanner 102, align the scan image with the 2D or 3D human model of the patient, and render the aligned image and 2D or 3D model visually (e.g., in an overlaid picture) to allow the scan image to be presented and analyzed with reference to anatomical characteristics (e.g., body shape and/or pose) of the patient as indicated by the model. This way, more insight may be gained into the organ(s) or tissue(s) of the patient captured in the scan image based on the additional information provided by the 2D or 3D model. For instance, the 2D or 3D model may indicate a position of the patient at the time the scan image is taken.

The alignment described above may be accomplished, for example, by identifying and matching respective anatomical landmarks (e.g., joint locations) in the scan image and the 2D or 3D model. The alignment may also be accomplished, for example, by determine a correlation (e.g., a spatial relationship) between a first coordinate system associated with the 2D or 3D model (e.g., with the sensing device 104) and a second coordinate system associated with a medical environment or a medical device, and use the correlation to match up corresponding areas of the scan image and the 2D or 3D model. The correlation between the two coordinate systems may be determined, for example, during system setup based on markers placed in the medical environment and/or by comparing sample images produced by the sensing device 104 and a concerned medical device (e.g., such as the medical scanner 102).

Using the 2D or 3D model as a common reference, the processing device 112 may be able to align multiple different scan images (e.g., from respective imaging modalities) of the patient together, for example, by aligning each scan image with the 2D or 3D model and thereafter aligning one scan image with another using the 2D or 3D model as an intermediate reference. When referred to herein, the alignment of two or more scan images or the alignment of a scan image with the 2D or 3D model may include overlaying one scan image with another scan image or overlaying the 2D or 3D model with the scan image.

By establishing a correlation between a 2D or 3D human model of a patient produced by the sensing device 104 and scan images of the patient obtained from other sources or modalities, the processing device 112 may determine a target scan or treatment area of a patient and indicate the target area to the patient or a medical professional administering a medical procedure for the patient. For example, the processing device may determine, based on preexisting scan images obtained from the other sources or modalities, that an organ of the patient (e.g., lungs, head, etc.) needs to be further scanned or treated. The processing device 112 may align one or more of the preexisting scan images with a 2D or 3D model of the patient (e.g., a 3D mesh of the patient) produced by the sensing device 104 and determine where the organ (e.g., the target scan area) is on the 3D mesh. The processing device 112 may indicate the determined target area to the patient or the medical professional visually, for example, by marking the target area on the 3D mesh. This way, localization of a target scan or treatment site may be accomplished in real time (e.g., while the patient is waiting to be scanned or treated), non-invasively, and/or without using radioactive tracers, and the results may be used to provide guidance to treatment planning, protocol design, and/or surgical navigation (e.g., to guide a surgical robot such as a built-in multiple-degrees-of-freedom (MDOF) robot or NIDOF robotic arms, for collision avoidance, etc.).

Based on a 2D or 3D human model of a patient produced by the sensing device 104, the processing device 112 may also be configured to identify a background object in a scan image of the patient, and segment or subtract the background object from the scan image so that the scan image may be analyzed without interference. For example, a scan image of the patient received by the processing device 112 (e.g., from the medical scanner 102) may include a scan bed in the background of the scan image. To segment or subtract the area or pixels of the scan image that correspond to the scan bed, the processing device 112 may determine a silhouette of the patient based on a 2D or 3D human model of the patient produced by the sensing device 102 while the patient is lying on the scan bed, and identify the area or pixels of the scan image that lie outside the silhouette as the area of pixels corresponding to the scan bed. The processing device 112 may then segment or subtract the area or pixels corresponding to the scan bed from the scan image and present the image resulting from the segmentation or subtraction for further analysis.

The processing device 112 may also utilize the 2D or 3D human model of a patient produced by the sensing device 104 to facilitate positioning of the patient during a scan or treatment procedure. For example, as described herein, the 2D or 3D human model of the patient may include a 3D mesh or contour of the patient and/or parameters that indicate a plurality of anatomical characteristics of the patient (e.g., the body shape of the patient, a pose of the patient, and/or a distance of the patient from the medical scanner 102, etc.). Based on these indications, the processing device 112 may determine, e.g., in real time (e.g., while the patient is still in the position or pose indicated by the 2D or 3D human model), whether the position or pose of the patient meets a predetermined protocol for the scan or treatment procedure. If the processing device determines that the position or pose of the patient does not meet the predetermined protocol, the processing device 112 may provide instructions (e.g., a command) to the patient and/or the medical professional administering the procedure for correcting the position or pose of the patient. The instructions may include visual and/or audio instructions including, for example, animations and/or presentations suitable for augmented reality (AR) devices. This way, the patient and/or the medical professional may visualize the differences between the patient's current position and a desired position (e.g., a guideline position) and make necessary adjustment to minimize or eliminate the differences.

The anatomical characteristics of the patient indicated by the 2D or 3D human model may also be used to determine a radiation consumption level of the patient. For example, the processing device 112 may estimate the height and/or weight of the patient as well as the distance between the patient and the medical scanner 102 based on the 2D or 3D human model of the patient, and use the estimation together with operating parameters of the medical scanner (e.g., strength of the magnetic field generated by the scanner, amount of energy released by the scanner, etc.) to calculate the amount radiation received by the patient. The processing device 112 may generate a report of the radiation level and/or provide an alert if the level exceeds a certain threshold.

The 2D or 3D human model of the patient produced by the sensing device 102 may also be used to determine an identity of the patient. For example, the processing device 112 may comprise or be coupled to a feature database comprising known visual features (e.g., keypoints indicating joint locations, joint angles, facial features, body shapes, positions, poses, walking patterns, etc.) of one or more patients. These known visual features or keypoints may be pre-computed and stored in the feature database. In response to receiving a 2D or 3D human model of the patient from the sensing device 102, the processing device 112 may match the visual features or keypoints comprised in the 2D or 3D human model with those stored in the feature database and determine the identity of the patient based on a matching score (e.g., higher scores indicate better matching).

Additionally or alternatively, the processing device 112 may utilize artificial neural networks trained for visual recognition to determine the identity of the patient. In examples, the neural networks may include a convolutional neural network (CNN) that comprises a cascade of layers each trained to make pattern matching decisions based on a respective level of abstraction of the visual characteristics contained in a set of images (e.g., in the pixels of the images). The training of the neural network may be performed using large amounts of imagery data and/or specific loss functions through which the neural network may learn to extract features (e.g., in the form of feature vectors) from a newly provided input image, determine whether the features match those of a known person, and indicate the matching results at an output of the neural network. Using one or more such neural networks, the processing device 112 may be configured to compare visual features of a patient indicated by or extracted from the 2D or 3D human model against those extracted from other images of the patient and determine the identity of the patient based on the comparison or matching.

Once determined, the identity of the patient may be used to personalize the healthcare services provided to the patient. For example, the processing device 112 may use the patient's identity to retrieve medical records associated with the patient from the repository 114, unify or synthesize the retrieved medical records with other information obtained about the patient (e.g., physical and/or anatomical characteristics of the patient indicated by the 2D or 3D human model), and present the unified or synthesized records to allow a more comprehensive review or analysis of the patient medical conditions.

As described herein, the processing device 112 may be communicatively coupled to other medical devices of the medical system 100 (e.g., the medical scanner 102). As such, the processing device 112 may be configured to control one or more of the other medical devices based on information acquired from the 2D or 3D human model of the patient produced by the sensing device 104. For example, upon determining the physical characteristics of the patient based on the 2D or 3D human model of the patient, the processing device 112 may transmit a command or control signal (e.g., to the medical scanner 102 or another device controlling the medical scanner 102) to adjust an operating parameter of the medical scanner 102, e.g., to better accommodate the patient. Such an operating parameter may be associated with, for example, the height of a scan bed, a scan angle, a dosage level, a position or orientation of the medical scanner, etc., and the command or control signal may be transmitted in digital and/or analog forms.

Further, although examples are provided herein for generating a 2D or 3D human model of a patient and using the model to improve the quality of healthcare services for the patient, it will be appreciated that the sensing device 104 may receive images of multiple patients and generate respective 2D or 3D human models (e.g., representations of the 2D or 3D models) for the patients based on these received images, for example, simultaneously. The images of the patients may be captured by a same sensor or by different sensors, and the generation of the 2D or 3D human models may be accomplished by a same functional unit or by different functional units. The sensing device 104 may be configured to be modular and/or extensible so that sensors and/or processors (e.g., GPUs) may be added to or removed from the sensing device to accommodate varying application requirements. The modularity and extensibility of the sensing device will be described in greater detail below.

The sensing device 104 may also be configured to receive images of an object and a scene present in a medical environment, analyze the images using the techniques described herein, and generate a 2D or 3D models of the object or scene or a report regarding the object or scene that may indicate a condition of the medical environment. For example, based on images of one or more objects captured by a sensor, the sensing device 104 may determine respective categories of the one or more objects and a number of items in each of the categories, wherein the categories may include at least one of medical tools, medicine, or food supplies. The sensing device 104 may transmit the information (e.g., in a report or a visual representation) to the processing device 112, which may use the information to automate or improve the efficiency of facility management such as inventory management, tool tracking, traffic control, etc. In examples, the information obtained via the sensing device 104 may indicate the condition in an operating room (e.g., the state of surgical tools or devices, an amount of blood loss of a patient, etc.) so that critical issues may be identified and addressed. In examples, the information obtained via the sensing device 104 may indicate that food or medical supply inventory at a location is running low so that replenishment may be ordered. In examples, the information obtained via the sensing device 104 may indicate that traffic in an area of the medical environment is heavy so that patients and medical staff may be informed to avoid the area.

The medical system 100 and/or the processing device 112 may comprise a display device 116 and/or an audio device (not shown), which may be configured to display the various commands, instructions, alerts and/or reports generated by the processing device 112 and/or other devices in the system, as described herein. The display device 116 may include one or more monitors (e.g., computer monitors, TV monitors, tablets, mobile devices such as smart phones, etc.), one or more speakers, one or more augmented reality (AR) devices (e.g., AR goggles), and/or other accessories configured to facilitate audio or visual presentations. The display device 116 may be communicatively coupled to the processing device 112 and/or the sensing device 104 via the communication network 108 or another suitable communication link. As described herein, the information or instructions presented via the display device 116 may include desired positions and poses of a patient for a medical procedure, positions taken by the patient during past scans, adjustment instructions for the patient to get into the desired positions or poses, surgical navigation instructions, dosage consumption levels, etc. The information and/or instructions may be presented to the patient 106 in various formats including, for example, audios, videos, animations, AR presentations, etc.

Figure 2:
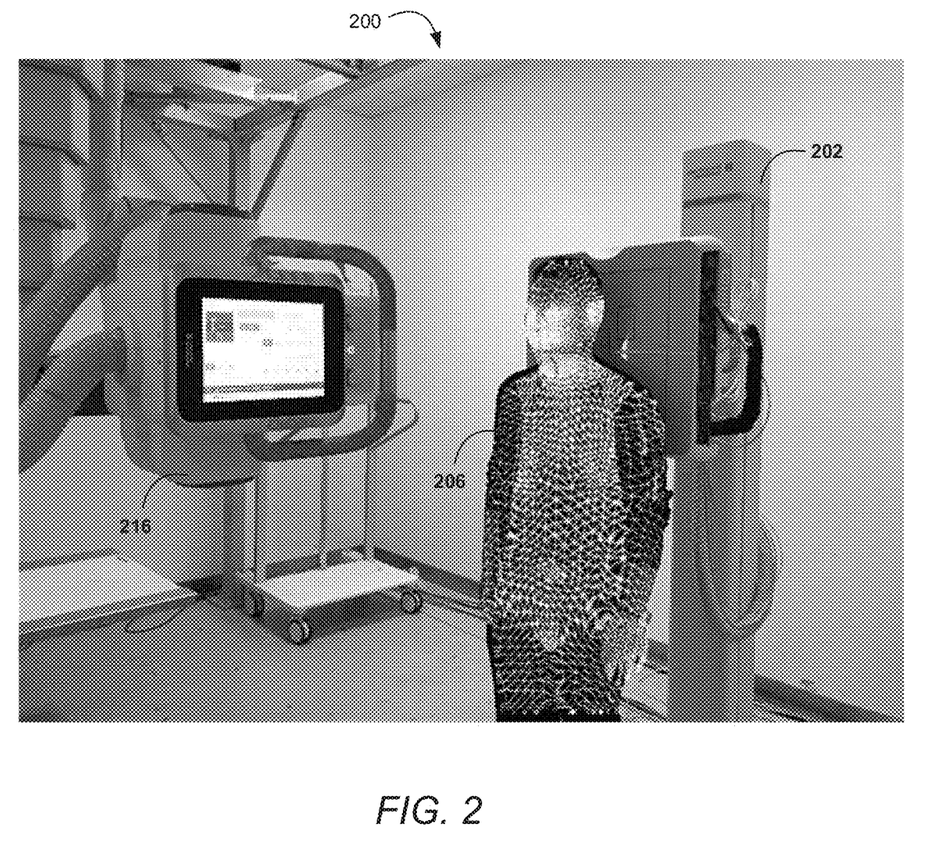
FIG. 2 is a simplified diagram illustrating how a sensing device as described herein may be facilitate the operation of a medical system.

The systems, methods and instrumentalities described herein may be further illustrated by FIG. 2, which shows an example medical environment (e.g., a scan room 200) in which a sensing device (e.g., the sensing device 104 shown in FIG. 1) may be installed. As shown, the scan room 200 may be equipped with a medical scanner 202 (e.g., the medical scanner 102 shown in FIG. 1) such as an upright X-ray scanner and a display device 216 (e.g., the display device 116 shown in FIG. 1). The display device 216 may be communicatively coupled to the medical scanner 202. (e.g., via a wired or wireless communication network) or be a part of the medical scanner 202. A sensing device (not shown in FIG. 2) such as the sensing device 104 of FIG. 1 may be added to the scan room 200 (e.g., installed on a wall, attached to a hanging mount off the ceiling, placed on a shelf, etc.) and configured to generate a 2D or 3D human model such as a 3D mesh of a patient 206 while the patient is standing in front of the medical scanner 101. As described herein, the 2D or 3D human model may be generated based on one or more images (e.g., photos or thermal images) of the patient captured by a sensor (e.g., a camera, a thermal sensor, etc.) comprised in the sensing device or by one or more sensors already installed in the scan room 202 (e.g., existing sensors that are external to the sensing device). A functional unit (e.g., which may comprise one or more processors) of the sensing device may receive these images of the patient, analyze the images to determine a plurality of features that is representative of one or more anatomical characteristics (e.g., joint locations, joint angles, etc.) of the patient, and estimate the 2D or 3D human model of the patient based on the plurality of features. The 2D or 3D human model may indicate the one or more physical characteristics of the patient such as the body shape and/or pose of the patient, position of the patient relative to the medical scanner 202, and/or other anatomical features of the patient.

The 2D or 3D human model may be estimated and transmitted in real time (e.g., while the patient is standing in front of the medical scanner 101) in one or more data streams to a processing device (e.g., the processing device 112 shown in FIG. 1), which may be located inside the scan room 200 or remotely from the scan room 200. The transmission may be performed, for example, via a communication circuit of the sensing device, and, in addition to the 2D or 3D human model, the one or more data streams may also include the images of the patient (e.g., raw image data such as pixel data) produced by the sensors. In response to receiving the 2D or 3D human model generated by the sensing device and/or the images produced by the sensors, the processing device may render the 2D or 3D human model and/or the images of the patient in a way that allows the information to be used to improve various aspects of a healthcare service provided to the patient 206 including, e.g., unified or coordinated medical diagnosis, guided imaging or surgical procedures, patient positioning and/or monitoring, medical facility management, and/or the like. For example, the processing device may overlay an image of the patient with the 2D or 3D human model (e.g., a 3D mesh) of the patient, as shown in FIG. 2, so that a target scan site of the patient may be determined and the medical scanner may be controlled (e.g., remotely and/or automatically) to focus on the target scan site (e.g., to collimate X-ray beams towards the target scan site to reduce radiation, improve subject contrast and image quality, etc.). As another example, the 2D or 3D human model may be used to identify, detect, and/or track the movements and activities of a patient or an object in the medical environment for purposes of process monitoring, process optimization, resource pre-allocation, resource utilization analysis, automated process logging, workflow analysis and optimization, automated process cost code estimation, etc.

Figure 3:
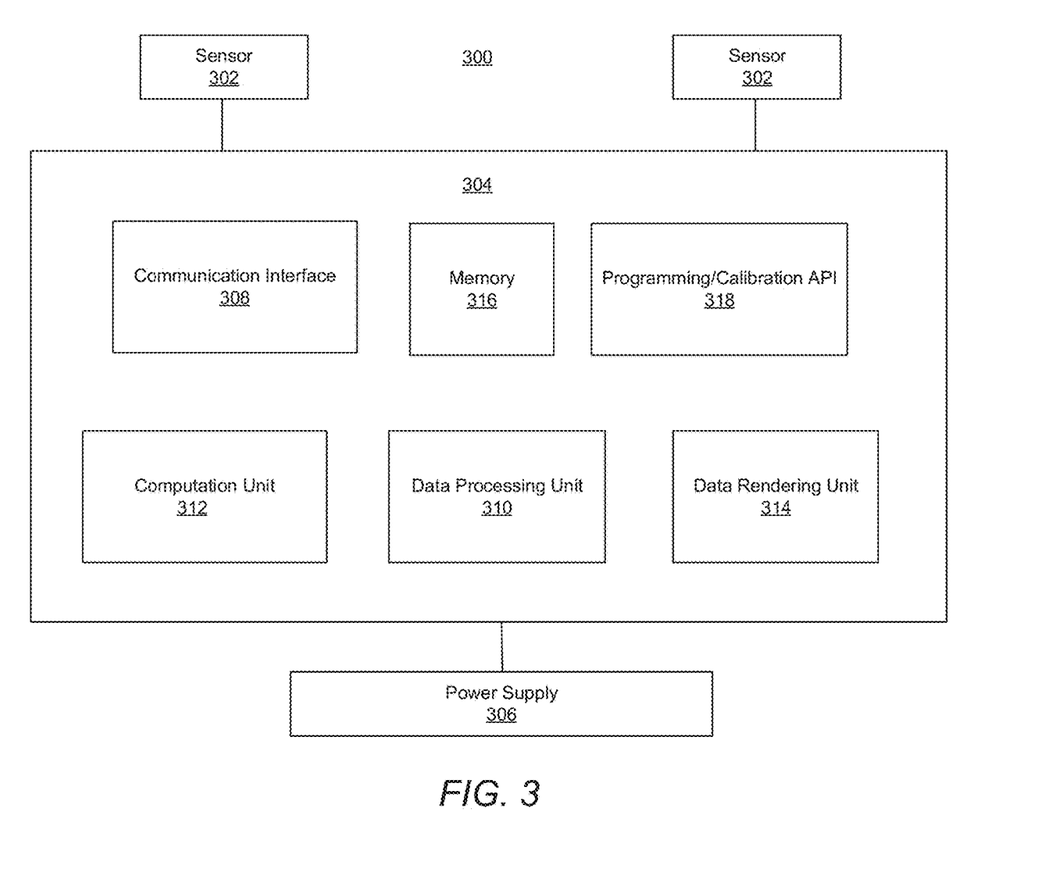
FIG. 3 is a simplified block diagram illustrating an example sensing device as described herein.

FIG. 3 illustrates an example sensing device 300 (e.g., the sensing device 104 shown in FIG. 1) that may be placed or installed in a medical system such as the medical system 100 described herein. The sensing device 300 may comprise a sensor 302, a functional unit 304, and a power supply that are configured to be hosted in a housing. Although two sensors are shown in the figure, it will be appreciated that the sensing device 300 may comprise any number of sensors, or the sensing device 300 may not comprise any sensor and may instead be configured to receive images from an external sensor (e.g., an existing sensor in a medical system). Further, although one or more of the components are shown in FIG. 3 as being inside or outside of the functional unit 304, these components are not restricted to the configuration shown in the figure and may be moved inside or outside of the functional unit 304 without affecting the functionalities of the sensing device described herein.

As described herein, the sensor 302 may include a RGB sensor, a depth sensor, a RGB plus depth (RGB-D) sensor, a thermo sensor such as a FIR or NIR sensor, a radar sensor, a motion sensor, a camera (e.g., a digital camera) and/or other types of image capturing circuitry configured to generate images (e.g., 2D images or photos) of a person, object, and/or scene in the FOV of the sensor. And the images generated by the sensor 302 may include, for example, one or more photos, thermal images, and/or radar images of the person, object or scene. Each of the images may comprise a plurality of pixels that collectively represent a graphic view of the person, object or scene and that may be analyzed to extract features that are representative of one or more characteristics of the person, object or scene.

The sensor 302 may be communicatively coupled to the functional unit 304, for example, via a wired or wireless communication link. In examples, the sensor 302 may be configured to transmit images generated by the sensor to the functional unit 304 (e.g., via a push mechanism). In examples, the functional unit 304 may be configured to retrieve images from the sensor 302 (e.g., via a pull mechanism). The transmission and/or retrieval may be performed on a periodic basis (e.g., based on a preconfigured schedule) or in response to receiving a control signal triggering the transmission or retrieval. Such a control signal may be sent, for example, by the sensor 302, e.g., when an image has become available, or by a remote control device such as a mobile device or a system controller, e.g., upon receiving an input from a user.

The sensor 302 may be configured to receive one or more control signals (e.g., digital control messages) from the functional unit 304 that may affect the operation of the sensor 302. For example, the sensor 302 may receive a command from the functional unit 304 to adjust the FOV of the sensor (e.g., by manipulating a direction or orientation of the sensor). As another example, the sensor 302 may receive a command from the functional unit 304 that changes the resolution at which the sensor takes images of a person, object or scene.

The sensor 302 and/or the functional unit 304 (e.g., one or more components of the functional unit 304) may be powered by the power supply 306, which may comprise an alternative current (AC) power source or a direct current (DC) power source (e.g., a battery power source). When a DC power source such as a battery power source is used, the power supply 306 may be rechargeable, for example, by receiving a charging current from an external source via a wired or wireless connection. For example, the charging current may be received by connecting the sensing device 300 to an AC outlet via a charging cable and/or a charging adaptor (including a USB adaptor). As another example, the charging current may be received wirelessly by placing the sensing device 300 into contact with a charging pad.

The functional unit 304 may comprise one or more of a communication interface circuit 308, a data processing unit 310, a computation unit 312, a data rendering unit 314, a memory 316, or a programming and/or calibration application programming interface (API) 318. It should be noted that the architecture shown in FIG. 3 is provided merely as an example and is not meant to limit the scope of the disclosure to such an architecture. For example, the functional unit 304 is not restricted to including the exact components as shown in FIG. 3. Two or more of the components (e.g., functionalities of the components) may be combined, any one of the components may be divided into sub-components, any one of the components may be omitted, more components may be added, etc. As such, even though the functionalities of the sensing device 300 are described herein as being associated with respective one or more of the components, it will be appreciated that those functionalities may also be performed by a different component and/or be divided among multiple other components.

In the example shown in FIG. 3, the functional unit 304 may be configured to receive or retrieve images of a patient from the sensor 302 via the communication interface circuit 308, which may include one or more wired and/or wireless network interface cards (NICs) such as ethernet cards, WiFi adaptors, mobile broadband devices (e.g., 4G/LTE/5G cards or chipsets), etc. In examples, a respective NIC may be designated to communicate with a respective sensor. In examples, a same NIC may be designated to communication with multiple sensors.

The images received or retrieved from the sensor 302 may be provided to the data processing unit 310, which may be configured to analyze the images and estimate (e.g., construct or recover) models based on the images to depict (e.g., mathematically and/or visually) one or more characteristics (e.g., body shape, pose, etc.) of the patient depicted in the images. For example, the data processing unit 310 may be configured to analyze at least one of the images produced by the sensor 302. (e.g., at a pixel level), identify a plurality of features that is representative of one or more anatomical or physical characteristics of the patient, and estimate parameters (e.g., mesh parameters) that may be used to construct a human model (e.g., a parametric human model) of the patient. In examples, the plurality of features may represent joint locations and/or joint angles of the patient as depicted in the at least one image produced by the sensor 302, and the human model may include a SMPL model defined by a plurality of parameters that indicates one or more characteristics of the patient. The parameters estimated by the data processing unit 310 may include one or more shape parameters, $\beta$, and/or one or more pose parameters, $\theta$. The shape parameters may comprise coefficients of a principal component analysis (PCA) space that may be used to determine (e.g., recover) a blend shape of the patient. The pose parameters may be derived based on the locations and/or angles of a plurality of joints of the patient recovered from the at least one image (e.g., 23 joints comprised in a skeletal rig as well as a root joint), and may indicate a pose of the patient. Based on the shape and/or pose parameters (e.g., a set of 72 parameters corresponding to the 23 joints), the data processing unit 310 may determine a plurality of mesh vertices that may be used to generate a representation (e.g., a 3D mesh) of the 2D or 3D human model constructed for the patient. In addition, the data processing unit 310 may also be configured to use the shape/pose parameters and/or the features extracted from the at least one image to determine an identity of the patient. The data processing unit 310 may indicate the identity of the patient to other devices or components of the medical system to personalize the healthcare services provided to the patient.

The functionality of the data processing unit 310 may be facilitated by the computation unit 312, which may be configured to perform various computation intensive tasks such as feature extraction and/or feature classification based on the images produced by the sensor 302. The computation unit 312 may comprise one or more neural networks such as one or more convolutional neural networks (CNNs) and/or one or more deep neural networks (DNNs) trained for visual recognition. The neural networks may comprise multiple layers (e.g., an input layer, one or more convolutional layers, one or more non-linear activation layers, one or more pooling layers, one or more fully connected layers, and/or an output layer). Each of the layers may correspond to a plurality of filters (e.g., kernels) and each filter may be designed to detect a set of keypoints that collectively represent a respective visual feature or pattern. The filters may be associated with respective weights that, when applied to an input, produce an output indicating whether certain visual features or patterns have been detected. The weights associated with the filters may be learned by the neural networks through a training process that comprises inputting a large number of images from one or more training datasets to the neural network (e.g., in a forward pass), calculating losses resulting from weights currently assigned to the filters (e.g., based on a loss function such as a margin based loss function), and updating (e.g., in a backward pass) the weights assigned to the filters so as to minimize the losses (e.g., based on stochastic gradient descent). Once trained, the neural networks may take an image at the input layer, extract and/or classify visual features or patterns from the image (e.g., in the form of feature vectors), and provide an indication at the output layer for whether an extracted feature matches a known feature and/or whether the extracted feature falls within a specific category or class.

In addition to or in lieu of the neural networks described above, the computation unit 312 may comprise or may be coupled to a feature database configured to store a plurality of known features of the patient (e.g., facial features, body shapes, body contours, joint locations, joint angles, walking patterns, poses, etc.). Each feature may correspond a combination of keypoints arranged in a specific manner in the images such as points at which the direction of the boundary of an object changes abruptly, intersection points between two or more edge segments, etc. The keypoints may be characterized by well-defined positions in the image space and/or stability to illumination or brightness perturbations. Accordingly, these keypoints may be identified based on image derivatives, edge detection, curvature analysis, and/or the like. And once identified, the keypoints and/or the feature represented by the keypoints may be described with a feature descriptor or feature vector. In an example implementation of such feature descriptors or vectors, information related to the feature (e.g., appearance of the local neighborhood of each keypoint) may be represented by (e.g., encoded into) a series of numerical values stored in the feature descriptors or vectors. The descriptors or vectors may then be used as "fingerprints" for differentiating one feature from another or for matching one feature with another.

The one or more human models (e.g., parameters for constructing the human models) generated by the data processing unit 310 and/or the computation unit 312 may be provided to the data rendering unit 314, which may be configured to generate representations (e.g., 2D or 3D representations such as 2D or 3D meshes) of the human models that depict one or more anatomical or physical characteristics of the patient. For example, the data rendering unit 314 may receive a plurality of mesh vertices determined by the data processing unit 310 and/or the computation unit 312. Each of the vertices may in turn include respective position, normal, texture, and/or shading information. Based on these vertices, the data rendering unit 314 may create a 2D or 3D mesh of the patient, for example, by connecting multiple vertices with edges to form a polygon (e.g., such as a triangle), connecting multiple polygons to form a surface, using multiple surfaces to determine a 3D shape, and applying texture and/or shading to the surfaces and/or shapes. Once created, the 2D or 3D representation may be output by the data render unit 314 in one or more data streams to a receiving device (e.g., the processing device 112 in FIG. 1), for example, over the communication interface circuit 308. Further, in addition to the human model information generated by the data processing unit 310 and/or the computation unit 312, the data rendering unit 314 may also be configured to receive the original imagery data produced by the sensor 302 and output the original imagery data to the receiving device, for example, in a same or different data stream as the data stream carrying the representation.

Each of the data processing unit 310, the computation unit 312, or the data rendering unit 314 may comprise one or more processors such as a central processing unit (CPU), a graphics processing unit (GPU), a microcontroller, a reduced instruction set computer (RISC) processor, an application specific integrated circuit (ASIC), an application-specific instruction-set processor (ASIP), a physics processing unit (PPU), a digital signal processor (DSP), a field programmable gate array (FPGA), or a combination thereof. The data processing unit 310, computation unit 312, and/or data rendering unit 314 may also comprise other type(s) of circuits or processors capable of executing the functions described herein. Further, the data processing unit 310, the computation unit 312, or the data rendering unit 314 may utilize the memory 316 to facilitate one or more of the operations described herein. For example, the memory 316 may include a machine-readable medium configured to store data and/or instructions that, when executed, cause the processing unit 310, the computation unit 312, or the data rendering unit 314 to perform one or more of the functions described herein. Examples of a machine-readable medium may include volatile or non-volatile memory including but not limited to semiconductor memory (e.g., electrically programmable read-only memory (EPROM), electrically erasable programmable read-only memory (EEPROM)), flash memory, and/or the like. And even though not shown in FIG. 3, the sensing device 300 may also comprise one or more mass storage devices that include a magnetic disk such as an internal hard disk, a removable disk, a magneto-optical disk, a CD-ROM or DVD-ROM disk, etc., on which instructions and/or data may be stored to facilitate the performance of the functions described herein.

The sensing device 300 and/or the functional unit 304 may be configured to be modular and extensible such that sensors, communication circuits, data processing units, computation units, and/or data rendering units may be added to or removed from the sensing device 300, for example, to accommodate different system settings, configurations and/or requirements in a medical environment (e.g., the medical system 100). For example, if output quality is the priority in the medical environment, a high-resolution sensor (e.g., a high-resolution camera) may be included in (e.g., added to) the sensing device 300 to meet the priority. On the other hand, if the priority is on output speed (e.g., frame rate), a sensor (e.g., a camera) with lower resolution and/or a communication circuit with faster bitrates (e.g., an ethernet card rather than a WiFi card) may be used to meet the output requirement. As another example, the sensing device 300 may be configured to work (e.g., simultaneously) with multiple devices in the medical environment such as multiple imaging modalities (e.g., CT, MR, etc.), in which case the sensing device may include respective sets of sensors, communication circuits, power supplies, processors (e.g., data processing units, computation units, and/or data rendering units as described herein) for the respective medical devices. As yet another example, the sensing device 300 may be configured to receive images of multiple patients (e.g., from different sensors) and generate respective 2D or 3D models for the patients based on the images, for example, simultaneously. In such a scenario, the sensing device may include respective sets of sensors, communication circuits, power supplied, processors (e.g., data processing units, computation units, and/or data rendering units as described herein) for capturing and processing the respective images of the respective patients.

In examples, the sensing device 300 and/or the functional unit 304 may comprise multiple slots (e.g., expansion boards, etc.) each equipped with at least one of a power connector or a communication circuit (e.g., a network interface card, a USB port, etc.) capable of transmitting and receiving information over a wired or wireless communication link. Sensors and/or processors (e.g., data processing units, computation units, and/or data rendering units as described herein) may be hosted in (e.g., inserted into) these slots, upon which the sensors and/or processors may receive power through the respective power connectors and perform data exchange with one or more internal or external devices via the respective communication circuits. These sensors and processors may respectively possess similar capabilities as the sensor 302, the data processing unit 310, the computation unit 312, and the data rendering unit 314 described herein, and may be added to or removed from the sensing device 300, for example, to accommodate changing conditions and/or requirements in the medical environment in which the sensing device 300 is installed.

For example, the sensing device 300 may include a first set of one or more sensors configured to capture images of a first patient (e.g., a patient taking a X-ray scan) and a first set of one or more processors (e.g., the data processing unit 310, the computation unit 312, and the data rendering unit 314) configured to generate a first 2D or 3D model for the first patient and provide the model to a first receiving device (e.g., a controller associated with the X-ray scanner), The first set of one or more sensors and/or the first set of one or more processors may be hosted in a first slot of the sensing device 300, which may provide power and/or communication service to the sensors and/or processors. The sensing device 300 may also include a second slot configured to host (e.g., provide power and/or communication service to) a second set of one or more sensors and/or a second set of one or more processors (e.g., units similar to the data processing unit 310, the computation unit 312, and the data rendering unit 314). Such a second set of sensors may be configured to capture images of a second patient (e.g., a patient taking a CT scan) and the second set of one or more processors may be configured to generate a second 2D or 3D model for the second patient and provide the model to a second receiving device (e.g., a controller associated with the CT scanner) In this manner, the sensing device 300 may be modular and extensible to handle data processing tasks associated with different patients and/or imaging modalities. In other example situations such as when the amount of computation, communication, and/or data storage workload approaches or exceeds the capabilities of one set of sensors and/or processors, more of the sensors and/or processors may be added to share the workload.

The operation of the sensing device 300 may be configured and/or controlled through the programming/calibration API 318, for example, using a remote programming device such as the programming device 110 in FIG. 1. In examples, the programming/calibration API 318 may be configured to receive commands (e.g., one or more digital messages) from the programming device that change the operating parameters of the sensing device 300 such as the orientation and/or FOV of a sensor, a resolution at which a sensor captures images, a quality required of a representation of a 2D or 3D model of a patient generated by the sensing device, a periodicity at which images are received or retrieved from a sensor, a bit rate at which the sensing device transmits a 2D or 3D human model of a patient and/or the original imagery data captured by a sensor, etc. In response to receiving a command from the programming device, the sensing device 300 (e.g., the functional unit 304) may adjust one or more aspects of its operation in accordance with the command. For instance, if the command specifies a higher output quality, the sensing device 300 may output a high-resolution mesh in response, and if the command specifies a higher frame rate, the sensing device 300 may output a lower-resolution mesh, but at an increased frame rate.

The sensing device 300 (e.g., the functional unit 304) may also be configured to receive ad hoc commands through the programming/calibration API 318, Such ad hoc commands may include, for example, a command to zoom in or zoom out a sensor, a command to reset the sensing device 300 (e.g., restart the device or reset one or more operating parameters of the device to default values), a command for the sensing device 300 to transmit or re-transmit certain types of data such as the meta-data relating to a human mesh generated by the sensing device (e.g., estimated parameters for constructing the human mesh) to a receiving device, a command to enable or disable a specific functionality of the sensing device 300 such as whether the sensing device should attempt to determine the identity of a patient, etc. The sensing device 300 (e.g., the functional unit 304) may also be programmed and/or trained (e.g., over a network) via the programming/calibration API 318. For example, the sensing device 300 may receive training data and/or operating logics through the programming/calibration API 318 during and/or after an initial configuration process.

The sensing device 300 (e.g., the functional unit 304) may be calibrated with the medical environment in which the sensing device is installed and/or with one or more other devices in the medical environment such as the medical scanner 102 in the medical system 100. The calibration may be performed, for example, during initial configuration of the sensing device 300 and/or in response to receiving a calibration command via the programming/calibration API 318. The calibration may include determining a relationship (e.g., spatial relationship) between a first coordinate system associated with the sensing device 300 and a second coordinate system associated with the medical environment or a medical device in the medical environment (e.g., such as the medical scanner 102. In FIG. 1). In examples, the sensing device 300 (e.g., the functional unit 304) may be configured to determine (e.g., learn) the spatial relationship between the first and second coordinate systems based on an offset between the respective origins of the two coordinate systems and/or a rotation angle between respective X or Y axes of the two coordinate systems. The sensing device 300 may receive information regarding such an offset and/or rotational angle via a configuration message (e.g., transmitted by a programming device). In examples, the sensing device 300 may be configured to learn the offset and/or the rotational angle by comparing sample images generated by the sensing device and the medical scanner, for example, based on annotated or marked areas of the images. In examples, the sensing device 300 may be configured to learn the offset and/or the rotational angle based on markers placed in the medical environment such as one or more objects placed in the corners of a scan room (e.g., during a calibration process).

Once the spatial relationship (e.g., spatial correlation) between the first and second coordinate systems are determined, the sensing device 300 and/or other devices in the medical system may utilize the spatial relationship for human model recovery, scan image analysis, and/or the like. For example, the sensing device 300 may receive an image of a patient from a sensor (e.g., a camera) that includes a scan bed in the background of the image, and the sensing device 300 may have knowledge about the location of the scan bed in the scan room as defined by the coordinate system of the scan room (e.g., the sensing device may have learned or been given the location of the scan bed during system configuration). If the sensing device 300 can determine the spatial relationship between the coordinate system of the scan room and the coordinate system of the sensor that captures the image, the sensing device 300 may convert the location of the scan bed in the former coordinate system (e.g., associated with the scan room) to a location in the latter coordinate system (e.g., associated with the sensing device or the sensor), for example, using a transformation matrix, based on the offset and/or rotational angle described herein, etc. The sensing device 300 may then be able to segment the scan bed from the image such that a 2D or 3D model may be generated just for the patient (e.g., excluding the scan bed from the model).

The spatial relationship (e.g., spatial correlation) between a first coordinate system associated with the sensing device 300 (e.g., a sensor of the sensing device) and a second coordinate systems associated with a medical device (e.g., the medical scanner 102 in FIG. 1) may also be used by a processing device or controller associated with the medical device to process or analyze medical information collected for a patient via the medical device together with a 2D or 3D human model of the patient generated by the sensing device 300. For example, based on the spatial correlation between the respective coordinate systems associated with the sensing device 300 and the medical scanner 102, a processing device or controller associated with the medical scanner 102 may be able to project a scan image of the patient captured by the medical scanner 102 onto the 2D or 3D human model of the patient generated by the sensing device 300 to allow for unified analysis of the scan image, as described herein.

Although the description of the sensing device 300 is provided using images of a patient as an example, it will be appreciated that similar techniques can also be used by the sensing device 300 to process images of an object or a scene. As described herein, information extracted from images of an object or scene may be used for various facility management purposes in a medical environment including, for example, inventory management, tool tracking, traffic control, facilitate monitoring, and/or the like.

Figure 4:
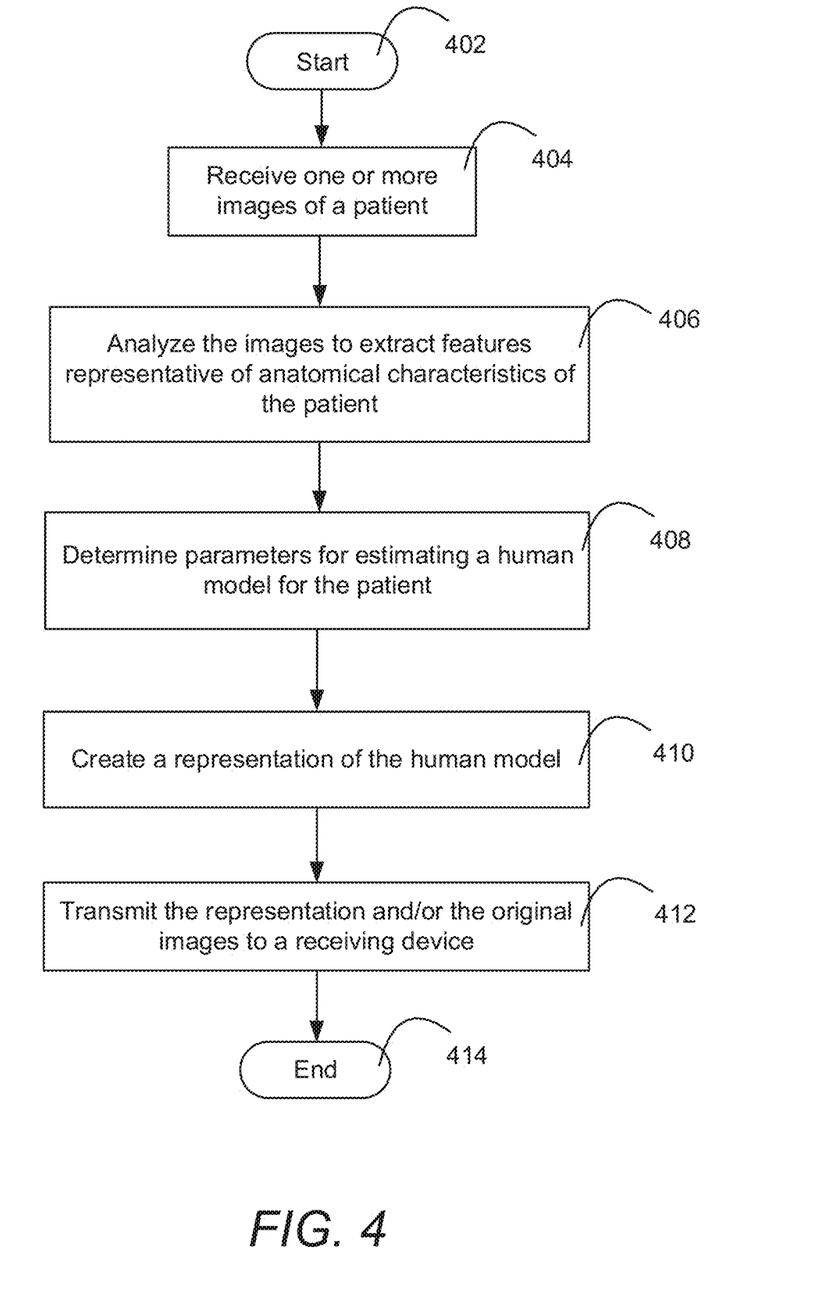
FIG. 4 is a flow diagram illustrating the operations of a sensing device as described herein.

FIG. 4 is a flow diagram illustrating example operations that may be performed by a sensing device (e.g., the sensing device 104 in FIG. 1 or the sensing device 300 in FIG. 3) as described herein. The sensing device may be configured to start the example operations at 402 periodically, for example, based on a predetermined time interval, upon receiving a command to start the operations, or in response to a patient being detected in medical environment. At 404, the sensing device may receive one or more images of the patient captured by a sensor such as an RGB sensor, a thermal sensor, or a digital camera. As described herein, the sensor may be an existing sensor (e.g., an existing camera) in the medical environment or may be a sensor comprised in the sensing device. At 406, the sensing device may analyze the received images and extract a plurality of features (e.g., in the form of feature vectors) that is representative of one or more anatomical characteristics of the patient as depicted in the one or more images. The features may represent, e.g., joint locations and/or joint angles of the patient.

Based on the extract features, the sensing device may determine estimate) a set of parameters relating to a human model of the patient at 408, for example, by recovering a shape of the patient and/or a plurality of joint angles of the patient based on the extracted features. The set of parameters may include, for example, one or more shape parameters that collectively indicate a body shape of the patient and one or more pose parameters that collectively indicate a pose of the patient. Utilizing the shape and/or pose parameters a set of 72 parameters corresponding to 23 joints of the patient), the sensing device may create a representation (e.g., a 2D or 3D mesh) of the human model at 410, for example, by determining a plurality of vertices of a mesh associated with the human model and create the mesh using the vertices. At 412, the sensing device may transmit the human model (e.g., the mesh) and/or the images received at 404 to a receiving device. The set of operations of the sensing device may then end at 414.

For simplicity of explanation, the operations of the sensing device are depicted in FIG. 4 and described herein with a specific order. It should be appreciated, however, that these operations may occur in various orders, concurrently, and/or with other operations not presented or described herein. Furthermore, not all illustrated operations may be required to be performed by the sensing device.

Figure 5:
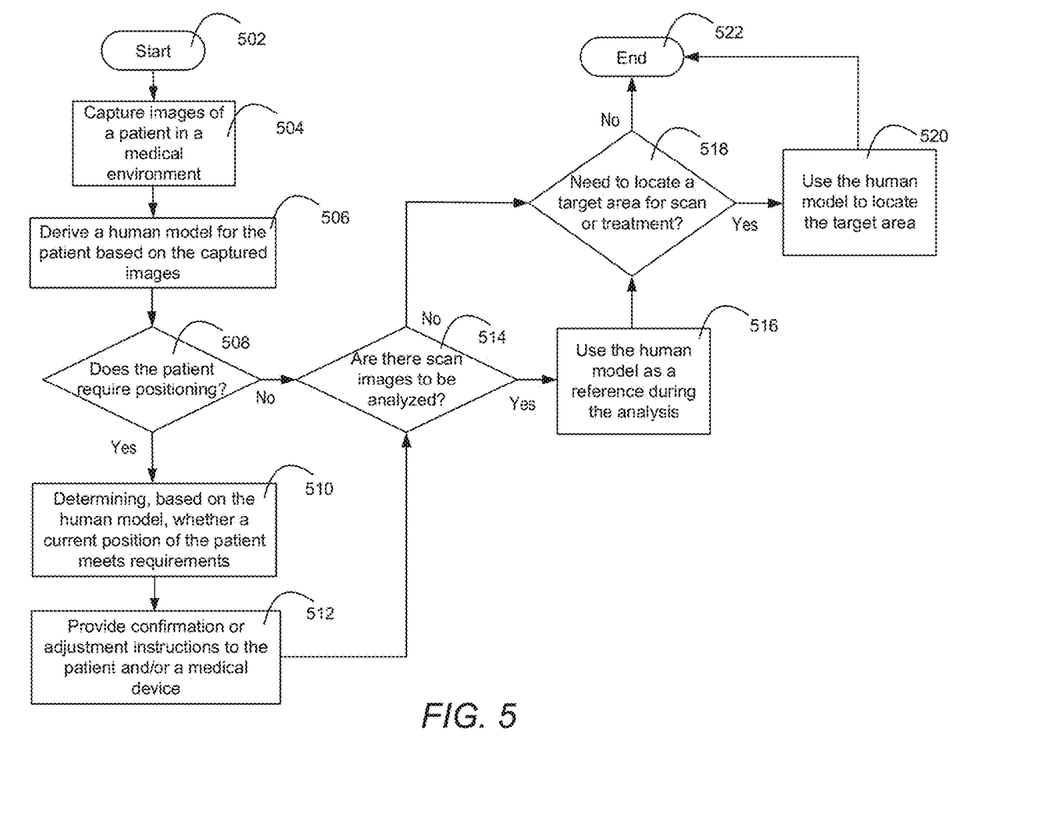
FIG. 5 is a flow diagram illustrating the operations of a medical system as described herein.

FIG. 5 is a flow diagram illustrating example operations that may be performed by one or more devices of a medical system (e.g., the medical system 100 in FIG. 1) as described herein. The operations may start periodically at 502. At 504, images of a patient may be captured in a medial environment, for example, by a sensing device (e.g., the sensing device 100 or 300) or by an existing sensor (e.g., an existing camera) the medical environment. At 506, a human model may be derived based on the images of the patient captured at 504. As described herein, such a human model may be derived by the sensing device and may be represented by a 2D mesh, a 3D mesh, a 2D contour, a 3D contour, etc. that indicates one or more anatomical or physical characteristics (e.g., shape, pose, etc.) of the patient as depicted in the captured images.

At 508, a determination may be made regarding whether the patient needs to be positioned for an upcoming medical procedure. If the determination is that the patient requires positioning, a further determination may be made at 510 based on the derived human model about whether a current position of the patient as indicated by the human model meets the requirements of a protocol designed for the medical procedure. If the current position of the patient meets the requirements, a confirmation may be provided at 512 to the patient and/or a medical professional overseeing the medical procedure. Otherwise, adjustment instructions (e.g., commands) may be provided to the patient at 512 to help the patient move into the required position. Adjustment instructions (e.g., control signals) may also be provided to the medical device involved in the procedure to alter one or more relevant operating parameters (e.g., height of a scan bed) of the device.

After the operation at 512 or if the determination at 508 is that the patient does not require positioning, another determination may be made at 514 regarding whether there are scan images of the patient that need to be analyzed. If the determination is that there are scan images to be analyzed, the scan images may be analyzed at 516 using the human model as a reference. For instance, one or more of the scan images may be aligned with the human model and/or with each other based on common anatomical landmarks identified in the scan images and the human model. The aligned scan images may then be analyzed together to obtain a holistic view of the patient's medical conditions.

After the operation at 516 or if the determination at 514 is that there are no scan images to be analyzed, another determination may be made at 518 regarding whether a target area for scan or treatment needs to be located. If there is such a target area, the human model may be used to locate the area and/or provide navigation guidance towards the target area, for example, based on body structure information comprised in the human model. After the operation at 520 or if the determination at 518 is that there is no target area to be located, the set of operations may end at 522.

For simplicity of explanation, the operations of the medical system are depicted in FIG. 5 and described herein with a specific order. It should be appreciated, however, that these operations may occur in various orders, concurrently, and/or with other operations not presented or described herein. Furthermore, it should be noted that not all operations that the medical system is capable of performing are depicted in FIG. 5 and described herein. It should also be noted that not all illustrated operations may be required to be performed by the medical system.

Further, the medical environment described herein may include a fitness or rehab facility and the sensing device may be used to monitor and/or guide physical therapy/rehab, training, sports, etc. For example, the sensing device may be used in these settings to track the movements of a patient or athlete (e.g., in real time), compare the movements with guidelines/instructions, and suggest necessary adjustment to improve the training or rehab activities.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A sensing device for a medical environment, the sensing device comprising:
   a first set of one or more sensors configured to capture at least one image of a first patient while the first patient is present in the medical environment;
   a first set of one or more processors configured to:
      analyze the at least one image of the first patient captured by the first set of one or more sensors to extract a first plurality of features that is representative of one or more anatomical characteristics of the first patient as depicted by the at least one image of the first patient;
      estimate a first three-dimensional (3D) human model for the first patient based on the first plurality of features extracted from the at least one image of the first patient, wherein the first 3D human model is estimated by recovering a first plurality of joint angles of the first patient as depicted in the at least one image of the first patient and a shape of the first patient as depicted in the at least one image of the first patient; and
      generate a first representation of the estimated first 3D human model; and
   a first communication circuit configured to transmit the first representation of the estimated first 3D human model to a first receiving device so that a command is produced by the first receiving device based on the first representation of the estimated first 3D human model to guide or alert the first patient or another person, or control a medical device in the medical environment.

2. The sensing device of claim 1, wherein the first set of one or more sensors includes a digital camera and the at least one image of the first patient includes a picture of the first patient captured by the digital camera.

3. The sensing device of claim 1, wherein the first set of one or more sensors includes at least one of a thermal sensor or a red-green-blue (RGB) sensor, and wherein the at least one image of the first patient includes a thermal image of the first patient captured by the thermal sensor or an RGB image of the first patient captured by the RGB sensor.

4. The sensing device of claim 1, wherein the estimated first 3D human model of the first patient includes a parametric human body model of the first patient and the first representation of estimated first 3D human model includes a 3D mesh.

5. The sensing device of claim 4, wherein the first plurality of features extracted from the at least one image of the first patient is expressed with one or more feature vectors and the one or more anatomical characteristics of the first patient include at least one of a joint location or a joint angle of the first patient.

6. The sensing device of claim 1, wherein the first set of one or more processors is configured to use at least one trained convolutional neural network to analyze the at least one image of the first patient or estimate the first 3D human model for the first patient.

7. The sensing device of claim 1, further comprising a first slot and a second slot, wherein:
   the first slot is configured to host the first set of one or more sensors or the first set of one or more processors;
   the second slot is configured to host a second set of one or more sensors or a second set of one or more processors;
   the second set of one or more sensors is configured to capture at least one image of a second patient while the second patient is present in the medical environment; and
   the second set of one or more processors is configured to:
      analyze the at least one image of the second patient captured by the second set of one or more sensors to extract a second plurality of features that is representative of one or more anatomical characteristics of the second patient as depicted by the at least one image of the second patient;
      estimate a second 3D human model for the second patient based on the second plurality of features extracted from the at least one image of the second patient, wherein the second 3D human model is estimated by recovering a second plurality of joint angles of the second patient as depicted in the at least one image of the second patient and a shape of the second patient as depicted in the at least one image of the second patient; and
      generate a second representation of the estimated second 3D human model.

8. The sensing device of claim 7, wherein the first slot includes at least one of the first communication circuit or a first power connector configured to provide power to the first set of one or more sensors or the first set of one or more processors, and wherein the second slot includes at least one of a second communication circuit configured to transmit the second representation of the second 3D human model to a second receiving device or a second power connector configured to provide power to the second set of one or more sensors or the second set of one or more processors.

9. The sensing device of claim 8, wherein the first receiving device is associated with a first imaging modality of the medical environment and the second receiving device is associated with a second imaging modality of the medical environment, each of the first or second imaging modality is associated with at least one of a computer tomography (CT) scanner, a magnetic resonance (MR) scanner, or an X-Ray scanner.

10. The sensing device of claim 7, wherein the first representation of the estimated first 3D human model is generated for a first imaging modality of the medical environment and the second representation of the estimated second 3D human model is generated for a second imaging modality of the medical environment, each of the first or second imaging modality is associated with at least one of a computer tomography (CT) scanner, a magnetic resonance (MR) scanner, or an X-Ray scanner.

11. The sensing device of claim 1, wherein the first representation of the estimated first 3D human model of the first patient is used by the first receiving device to determine a position of the first patient relative to the medical device and wherein the command produced by the first receiving device is associated with adjusting the position of the first patient relative to the medical device or adjusting an operating parameter of the medical device based on the position of the first patient.

12. The sensing device of claim 1, wherein the first set of one or more processors is further configured to determine a spatial relationship between a first coordinate system associated with the first set of one or more sensors and a second coordinate system associated with the medical environment.

13. The sensing device of claim 12, wherein the first set of one or more processors is configured to determine the spatial relationship between the first and second coordinate systems based on information received from a remote programming device.

14. The sensing device of claim 12, wherein the first set of one or more processors being configured to analyze the at least one image of the first patient captured by the first set of one or more sensors comprises the first set of one or more processors being configured to segment a background object from the at least one image of the first patient based on the spatial relationship between the first coordinate system and the second coordinate system.

15. The sensing device of claim 1, wherein the first set of one or more processors is further configured to receive, from a remote programming device, one or more operating parameters associated with estimating the first 3D human model or generating the first representation of the estimated first 3D human model.

16. The sensing device of claim 1, wherein the first communication circuit is further configured to transmit the at least one image of the first patient to the first receiving device.

17. The sensing device of claim 1, wherein the first communication circuit is further configured to transmit a plurality of parameters associated with the estimated first 3D human model of the first patient to the first receiving device.

18. The sensing device of claim 17, wherein the first communication circuit is configured to transmit the plurality of parameters associated with the estimated first 3D human model of the first patient to the first receiving device in response to a command received from a remote programming device.

19. A sensing device for a medical environment, the sensing device comprising:
   a communication circuit configured to receive at least one image of a patient from a sensor; and
   one or more processors configured to:
      analyze the at least one image of the patient received from the sensor to extract a plurality of features that is representative of one or more anatomical characteristics of the patient as depicted by the at least one image of the patient;
      estimate a three-dimensional (3D) human model for the patient based on the plurality of features extracted from the at least one image of the patient, wherein the 3D human model is estimated by recovering a plurality of joint angles of the patient as depicted in the at least one image of the patient and a shape of the patient as depicted in the at least one image of the patient;
      generate a representation of the estimated 3D human model; and
      transmit, via the communication circuit, the representation of the estimated 3D human model to a receiving device.

20. A method implemented in a medical system, the method comprising:
   receiving, from a sensor, at least one image of a patient;
   analyzing the at least one image of the patient received from the sensor to extract a plurality of features that is representative of one or more anatomical characteristics of the patient as depicted by the at least one image of the patient;
   estimating a three-dimensional (3D) human model for the patient based on the plurality of features extracted from the at least one image of the patient, wherein the 3D human model is estimated by recovering a plurality of joint angles of the patient as depicted in the at least one image of the patient and a shape of the patient as depicted in the at least one image of the patient;
   generating a representation of the estimated 3D human model; and
   transmitting, via a communication circuit, the representation of the estimated 3D human model to a receiving device.

* * * * *